(12) United States Patent
Klun et al.

(10) Patent No.: US 12,247,001 B2
(45) Date of Patent: Mar. 11, 2025

(54) COMPOUNDS COMPRISING PERFLUORINATED GROUP, PHOTOINITIATOR GROUP, AND AMIDE LINKING GROUP

(71) Applicant: 3M INNOVATIVE PROPERTIES COMPANY, St. Paul, MN (US)

(72) Inventors: Thomas P. Klun, Lakeland, MN (US); Brandon R. Pietz, St. Paul, MN (US); Paul J. Homnick, Lake Elmo, MN (US); Christopher S. Lyons, St. Paul, MN (US); Chad M. Amb, Roberts, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 101 days.

(21) Appl. No.: 17/912,975

(22) PCT Filed: Apr. 22, 2021

(86) PCT No.: PCT/IB2021/053344
§ 371 (c)(1),
(2) Date: Sep. 20, 2022

(87) PCT Pub. No.: WO2021/229331
PCT Pub. Date: Nov. 18, 2021

(65) Prior Publication Data
US 2023/0129152 A1    Apr. 27, 2023

Related U.S. Application Data

(60) Provisional application No. 63/024,572, filed on May 14, 2020.

(51) Int. Cl.
| C07C 271/22 | (2006.01) |
| C07C 269/06 | (2006.01) |
| C08F 2/48 | (2006.01) |
| C09D 4/06 | (2006.01) |
| C09D 7/63 | (2018.01) |

(52) U.S. Cl.
CPC .......... *C07C 271/22* (2013.01); *C07C 269/06* (2013.01); *C08F 2/48* (2013.01); *C09D 4/06* (2013.01); *C09D 7/63* (2018.01); *C08J 2367/02* (2013.01)

(58) Field of Classification Search
CPC ... C07C 269/06; C07C 271/16; C07C 271/20; C07C 271/22; C08F 2/48; C08J 2367/02; C08J 7/18; C09D 4/06; C09D 7/63
See application file for complete search history.

(56) References Cited

U.S. PATENT DOCUMENTS

| 3,214,492 A | 10/1965 | Tocker et al. |
| 3,250,808 A | 5/1966 | Moore, Jr. et al. |
| 3,429,852 A | 2/1969 | Skoultchi et al. |
| 4,529,783 A | 7/1985 | Tsunoda et al. |
| 4,922,004 A | 5/1990 | Kohler et al. |
| 5,202,359 A | 4/1993 | McIntyre |
| 5,274,179 A | 12/1993 | Wu |
| 5,391,587 A | 2/1995 | Wu |
| 5,484,822 A | 1/1996 | Minns |
| 5,621,018 A | 4/1997 | Chabrecek et al. |
| 6,099,122 A | 8/2000 | Chabrecek et al. |
| 6,204,306 B1 | 3/2001 | Chabrecek et al. |
| 6,245,922 B1 | 6/2001 | Heilmann et al. |
| 7,012,160 B2 | 3/2006 | Hayashida et al. |
| 7,141,354 B2 | 11/2006 | Sakayori |
| 7,718,264 B2 | 5/2010 | Klun et al. |
| 8,658,248 B2 | 2/2014 | Anderson et al. |
| 8,742,175 B2 | 6/2014 | Zhang et al. |
| 9,551,110 B2 | 1/2017 | Jonckheree et al. |
| 9,587,127 B2 | 3/2017 | Herlihy et al. |
| 9,718,896 B2 | 8/2017 | Hari et al. |
| 9,718,961 B2 | 8/2017 | Corveleyn et al. |
| 2004/0067311 A1 | 4/2004 | Baudin et al. |
| 2005/0129852 A1 | 6/2005 | Baudin et al. |
| 2014/0287200 A1 | 9/2014 | Ito et al. |
| 2014/0295149 A1 | 10/2014 | Ito et al. |
| 2017/0371240 A1 | 12/2017 | Liu et al. |

(Continued)

FOREIGN PATENT DOCUMENTS

| CN | 101805419 B | 8/2012 |
| CN | 101812143 B | 8/2012 |
| CN | 102675490 A | 9/2012 |

(Continued)

OTHER PUBLICATIONS

US 10,451,966 B2, 10/2019, Liu et al. (withdrawn)
WO2015111765 translated (Year: 2015).*
Allen, "Photochemistry and Photoinitiator Properties of 4-Substituted Amidobenzophenones and Imidobenzophenones", Journal of Photochemistry and Photobiology A: Chemistry, vol. 99, No. 2-3, Oct. 1996, pp. 191-196.
Angiolini, "Photosensitizer/Photoinitiator Interactions in Copolymeric Systems Bearing Side-Chain Thioxanthone And α-Morpholino Acetophenone Moieties", Polymer, vol. 36, No. 21, 1995, pp. 4055-4060.

(Continued)

*Primary Examiner* — Jafar F Parsa
*Assistant Examiner* — Blaine G Doletski
(74) *Attorney, Agent, or Firm* — Carolyn A. Fischer

(57) ABSTRACT

Compound are described comprising a perfluorinated group bonded to at least one terminal photoinitiator group with an organic linking group comprising at least one amide moiety. The compound typically comprises the (e.g. Michael addition) reaction product of i) a compound comprising an acryl group and a photoinitiator group; and ii) an amino functional perfluorinated compound. Also described is a composition comprising at least one free-radically polymerizable (e.g. fluorinated) monomer, oligomer, or combination thereof; and the described fluorinated photoinitiator compound and methods.

19 Claims, 3 Drawing Sheets

(56) References Cited

U.S. PATENT DOCUMENTS

2020/0109106 A1 4/2020 Vange et al.

FOREIGN PATENT DOCUMENTS

| | | |
|---|---|---|
| CN | 104039853 A | 9/2014 |
| CN | 104610541 A | 5/2015 |
| CN | 109265345 A | 1/2019 |
| JP | 05310635 A | 10/2013 |
| JP | 2014129457 A | 7/2014 |
| KR | 2014-0003120 A | 1/2014 |
| WO | WO2015111765 * | 7/2015 |
| WO | 2016121706 A1 | 8/2016 |
| WO | 2017172390 A1 | 10/2017 |
| WO | 2018159135 A1 | 9/2018 |
| WO | 2020095258 A1 | 5/2020 |
| WO | 2020097319 A1 | 5/2020 |
| WO | 2021229338 A1 | 11/2021 |
| WO | 2021229340 A1 | 11/2021 |
| WO | 2021229348 A1 | 11/2021 |
| WO | 2021229547 A1 | 11/2021 |
| WO | 2021231068 A1 | 11/2021 |

OTHER PUBLICATIONS

Green, Industrial Photoinitiators, Commercial Photoinitiators, A Technical Guide, 2010, pp. 1-58.

Hu, "Photoreactions of Polymeric (Meth)acryloylethyl PhenylglyoxylatesReactivity in Solution and Film" Journal of Chem. Mater., Jul. 1997, vol. 9, pp. 3171-3175.

Hult, "Photocuring in Air Using a Surface-Active Photoinitiator", Abstracts of Papers of the American Chemical Society, 1984, vol. 187, pp. 329.

International Search Report for PCT Application No. PCT/IB2021/053344, mailed on Jul. 20, 2021, 5 pages.

Levitchev, "Electrochemical Properties of Photocurable Membranes for All-Solid-State Chemical Sensors", Fresenius' Journal of Analytical Chemistry, 1998, vol. 361, No. 3, pp. 252-254.

Liang, "Fluorinated Photoinitiators: Synthesis And Photochemical Behaviors", Progress In Organic Coatings, vol. 114, Jan. 2018, pp. 102-108.

Ma, "Synthesis of Novel Macrophotoinitiator for the Photopolymerization of Acrylate", Journal of Applied Polymer Science, 2014, vol. 131, No. 11, pp. 40352/1-40352/8.

Shibanov, "Synthesis and Initiating Activity of Radical Polymerization Photoinitiators", Ukrainskil Khimicheskii Zhurnal, 1990, vol. 56.5, pp. 531-536.

Xu, "A Fluorinated Photoinitiator for Surface Oxygen Inhibition Resistance", Macromolecules (Print), Jan. 2012, vol. 45, No. 3, pp. 1158-1164.

Zhang "A Fluorinated Compound Used as Migrated Photoinitiator in the Presence of Air", Polymer, Jan. 2015, vol. 71, pp. 93-101.

Zhang, "UV-Curable Photosensitive Silicone Resins Based on a Novel Polymerizable Photoinitiator And GO-Modified TiO2 Nanoparticles", Composites Part B: Engineering, vol. 140, May 2018, pp. 214-222.

* cited by examiner

COMPOUNDS COMPRISING PERFLUORINATED GROUP, PHOTOINITIATOR GROUP, AND AMIDE LINKING GROUP

SUMMARY

Although various photoinitiator compounds have been described, industry would find advantage in photoinitiator compounds that are compatible with fluorinated free-radically polymerizable materials.

In one embodiment, compounds are described comprising a perfluorinated group bonded to at least one terminal photoinitiator group with an organic linking group comprising at least one amide moiety.

In typical embodiments, the compound comprises the (e.g. Michael addition) reaction product of i) a compound comprising an acryl group and a photoinitiator group; and ii) an amino functional perfluorinated compound.

Also described is a composition comprising at least one free-radically polymerizable monomer, oligomer, or combination thereof; and the fluorinated photoinitiator compound described herein. In some favored embodiments, the at least one free-radically polymerizable monomer and/or oligomer is fluorinated.

Also described is a method of making a cured composition comprising providing a composition comprising at least one free-radically polymerizable monomer, oligomer, or combination thereof and a fluorinated photoinitiator compound, as described herein, and (e.g. UV) radiation curing the composition. In some embodiments, the method further comprises coating the polymerizable composition onto a substrate prior to radiation curing. In some embodiments, upon radiation curing the polymerizable composition forms a film or film layer.

DETAILED DESCRIPTION

Figure 1:
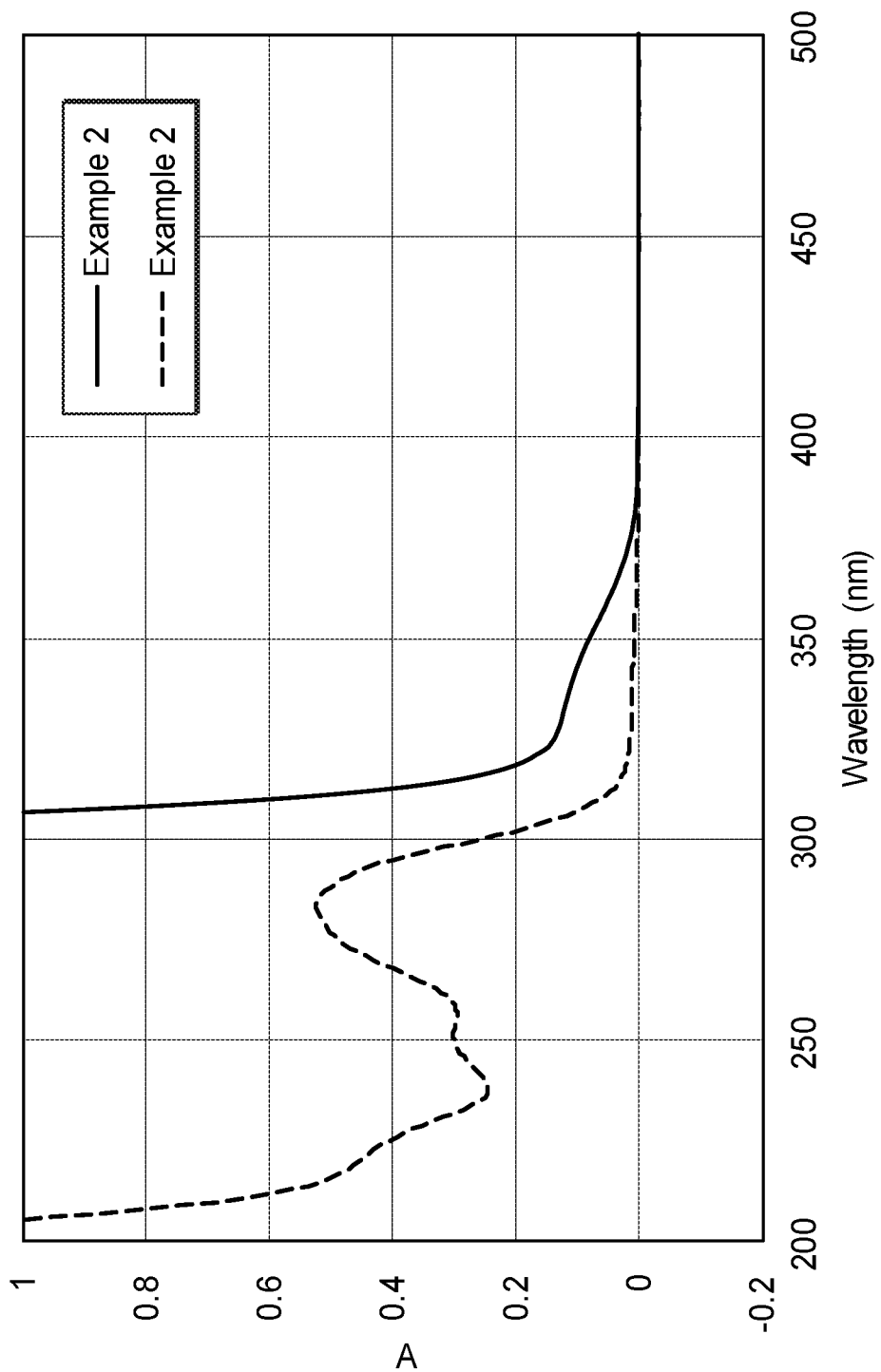
FIGS. 1-3 are graphs of absorbance (A) as a function of wavelength for illustrative fluorinated photoinitiator compounds comprising a perfluorinated group, photoinitiator group, and amide linking group. The solid lines represent a concentration of 0.1 wt. % in acetonitrile and the dashed lines represent a concentration of 0.01 wt. % in acetonitrile.

Presently described are compounds comprising a perfluorinated group bonded to at least one terminal photoinitiator group with an organic linking group comprising at least one amide moiety.

In typical embodiments, the compound has the following formula (Formula 1)

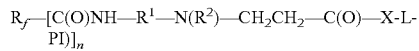

wherein
$R_f$ is a monovalent perfluorooxyalkyl group or divalent perfluoroxyalkylene group;
$R^1$ is an alkylene group optionally comprising one or more catenary oxygen atoms,
$R^2$ is H or an alkyl group of 1 to 4 carbon atoms;
X is —O—, —S—, or —NR$^3$—, wherein $R^3$ is H or an alkyl group of 1 to 4 carbon atoms;
L is a covalent bond or divalent organic linking group;
PI is a photoinitiator group; and
n is 1 when $R_f$ is a monovalent perfluorooxyalkyl group or n is 2 when $R_f$ is a divalent perfluorooxyalkylene group.

As used herein the term "catenary" refers to substituting a carbon atom of a carbon chain with a substituent (e.g. O or N). Thus, a pendent substituent (e.g. —OH) bonded to a carbon atom is not a catenary oxygen atom.

In some embodiments, the monovalent perfluorooxyalkyl group comprises moieties of 1 to 6 (e.g. linear or branched) perfluorinated carbon atoms and a single oxygen atom, such as $CF_3CF_2CF_2O$—. In some embodiments, the number of perfluorinated carbon atoms is at least 2 or 3. In some embodiments, the number of perfluorinated carbon atoms is no greater than 5 or 4.

In typical embodiments, the monovalent perfluorooxyalkyl group comprises perfluorinated poly(oxyalkylene) groups having repeat units of divalent perfluoroxyalkylene groups, having the general structure —$[C_mF_{2m}O]_s$—, wherein for each s, m independently ranges from 1 to 6. In some embodiments, m is at least 2 or 3. In some embodiments, the m is no greater than 5 or 4. In some embodiments, s is at least 2, 3, 4, 5, 6, 7, 8, 9, or 10. In some embodiments, s is no greater than 25, 24, 23, 22, 21, 20, 19, 18, 17, 16, 15, 14, 13, 12, 11, or 10.

In one embodiment, $R_f$ is "HFPO—". When n is 1 and $R_f$ is a monovalent perfluorooxyalkyl group, HFPO— refers to the end group $CF_3CF_2CF_2O$—$[CF(CF_3)CF_2O]_s$—$CF(CF_3)$— wherein s is an integer of 2 to 25, as previously described. HFPO— generally exist as a distribution or mixture of molecules with a range of values for s. Thus, s may be expressed as an average value. Such average value is typically not an integer.

In some embodiments, the divalent perfluoroxyalkylene group comprises moieties of 2 to 6 (e.g. linear or branched) perfluorinated carbon atoms and a single oxygen atoms such as —$CF_2$—$CF_2$—O—, —$CF(CF_3)$—$CF_2$—O—, —$CF_2$—$CF(CF_3)$—O—, —$CF_2$—$CF_2$—$CF_2$—O—, —$CF(CF_3)$—O—, and —$CF_2$—$CF_2$—$CF_2$—$CF_2$—O. In some embodiments, the number of perfluorinated carbon atoms is at least 2 or 3. In some embodiments, the number of perfluorinated carbon atoms is no greater than 5 or 4.

In typical embodiments, the divalent perfluorooxyalkyl group comprises perfluorinated poly(oxyalkylene) groups, having the general structure —$[C_mF_{2m}O]_s$— wherein for each s, m independently ranges from 1 to 6. In some embodiments, m is at least 2 or 3. In some embodiments, the m is no greater than 5 or 4. In some embodiments, s is at least 2, 3, 4, 5, 6, 7, 8, 9, or 10. In some embodiments, s is no greater than 25, 24, 23, 22, 21, 20, 19, 18, 17, 16, 15, 14, 13, 12, 11, or 10.

When n is 2 and $R_f$ is a divalent perfluorooxyalkyl group, —HFPO— refers to the group —$(CF_3)CF$—$[OCF_2(CF_3)CF]_s$—$O(CF_2)_pO$—$[CF(CF_3)CF_2O]_t$—$CF(CF_3)$—, wherein p ranges from 2 to 6 and s and t are independently integers of 2 to 25. In some embodiments p is 3 or 4. In some embodiments, the sum of s and t is at least 3, 4, 5, 6, 7, 8, 9, or 10. In some embodiments, the sum of s and t is no greater than 24, 23, 22, 21, 20, 19, 18, 17, 16, 15, 14, 13, 12, 11, or 10. Divalent —HFPO— generally also exists as a distribution or mixture of molecules with a range of values for s and t. Thus, the sum of s and t may be expressed as an average value. Such average value is typically not an integer.

Although Rf is preferably a monovalent perfluorooxyalkyl group or a divalent perfluoroxyalkylene group, Rf can alternatively be a perfluorinated alkyl or a perfluorinated alkylene group as known in art. The perfluorinated alkyl or a perfluorinated alkylene group typically comprises 2 to 6 perfluorinated carbon atoms. In some embodiments, the number of perfluorinated carbon atoms is at least 2 or 3. In some embodiments, the number of perfluorinated carbon atoms is no greater than 5 or 4.

Some representative compounds according to Formula 1 include:

Perfluorooxyalkyl and perfluoroxyalkylene compounds can be obtained by oligomerization of hexafluoropropylene oxide that result in terminal carbonyl fluoride group(s). The carbonyl fluoride group(s) may be converted to an ester by reactions known to those skilled in the art. Preparation of

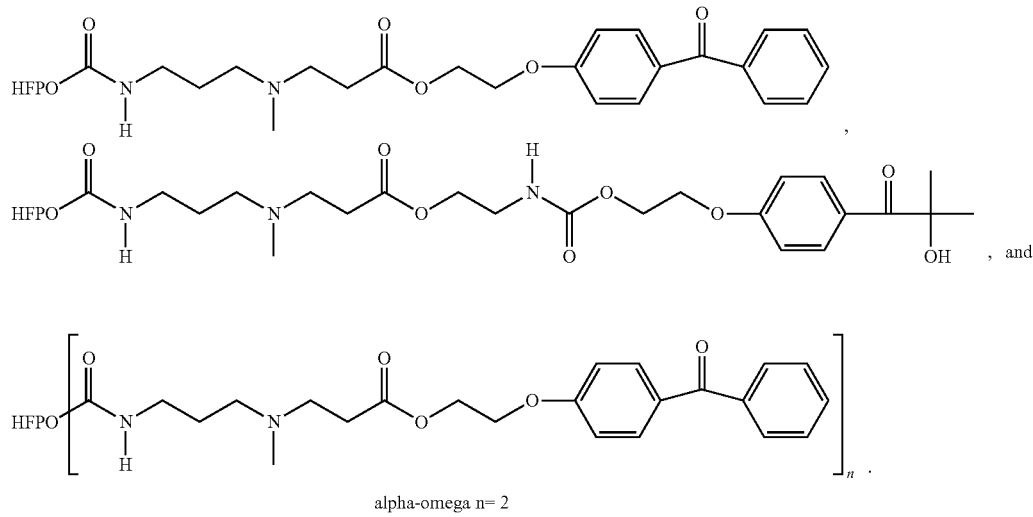

alpha-omega n= 2

The fluorinated photoinitiator compounds described herein can be prepared by any suitable method. In typical embodiments, such compounds comprise the (e.g. Michael addition) reaction product of i) an amino functional perfluorinated compound; and ii) a compound comprising an acryl group and a photoinitiator group. As used herein, "acryl" means acrylate, thioacrylate or acrylamide.

The fluorochemical compounds described herein may be prepared in a two-step process. The first step is the reaction of a perfluorinated methyl ester compound with a polyamine to produce the corresponding perfluorinated amine. The second step is Michael addition of the perfluorinated amines to the acryl group of the compound comprising an acryl group and a photoinitiator group.

For each step, the reactants are combined in a suitable solvent. When a homogeneous mixture or solution is obtained a catalyst is optionally added, and the reaction mixture is heated at a temperature, and for a time sufficient for the reaction to occur. Progress of the Michael addition reaction can be determined by monitoring the olefin concentration by use of $^1$H Fourier Transform Nuclear Magnetic Resonance (FT-NMR).

In some embodiments, a fluorinated solvent is utilized. Various partially fluorinated or perfluorinated solvents are known including perfluorocarbons (PFCs), hydrochlorofluorocarbons (HCFCs), perfluoropolyethers (PFPEs), and hydrofluorocarbons (HFCs), as well as fluorinated ketones and fluorinated alkyl amines. Such solvents are commercially available, for example, under the trade designation NOVEC from 3M Company, St. Paul, MN In other embodiments, the solvent is non-fluorinated, such as in the case of ketones such as acetone, methyl ethyl ketone (MEK), methyl isobutyl ketone, methyl amyl ketone and N-methyl pyrrolidone (NMP); ethers such as tetrahydrofuran, 2-methyl tetrahydrofuran and methyl tetrahydrofurfuryl ether; esters such as methyl acetate, ethyl acetate and butyl acetate; cyclic esters such as delta-valerolactone and gamma-valerolactone.

perfluorinated methyl ester compounds are described, for example, in U.S. Pat. Nos. 3,250,808 and 9,718,896.

An amino functional perfluorinated compound can be prepared by reaction of the terminal ester group(s) of the perfluorinated compound with a polyamine.

Useful polyamines comprise at least two amine groups. The amine groups are typically primary, secondary, or a combination thereof.

In some embodiments, the polyamine (e.g. diamine) comprises a terminal primary amine group (i.e. NH$_2$) and a terminal secondary amine group. Examples of such polyamines include H$_2$NCH$_2$CH$_2$CH$_2$N(CH$_3$)H, H$_2$NCH$_2$CH$_2$CH$_2$N(CH$_2$CH$_3$)H, H$_2$NCH$_2$CH$_2$CH$_2$CH$_2$CH$_2$CH$_2$N(CH$_3$)H, and

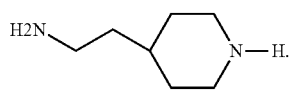

Primary amines exhibit greater reactivity with the ester group of the perfluorinated ester compound than secondary amines. The opposing secondary amine group of the polyamine (e.g. diamine) reacts with the acryl group of the compound comprising the photoinitiator group.

Various compounds comprising an acryl group and a photoinitiator group have been described in the literature. In some embodiments, the photoinitiator comprises a phenone group (i.e. an aromatic ketone containing a phenyl group directly attached to the carbonyl group). Representative phenone groups include for example benzophenone and acetophenone.

Some representative compounds comprising an acryl group and a (e.g. phenone) photoinitiator group are described as follows:

| Structure | L of Formula 1 | Reference |
|---|---|---|
| [acrylate-O-L-phenyl-C(O)-phenyl] | Covalent Bond<br>—CH₂CH(OH)CH₂O— or —CH₂CH(OH)CH₂C(O)O—<br>—CH₂CH₂O—<br>—CH₂CH₂OC(O)N(H)—(CH₂)₆—N(H)C(O)O— | U.S. Pat. No. 3,214,492<br>U.S. Pat. No. 3,429,852<br>U.S. Pat. No. 9,587,127<br>Zhang et. al. Compos. B. Eng., 2018, 140, 214-222 |
| [acrylate-O-L-phenyl-C(O)-C(CH₃)₂-OH] | Covalent bond<br>—CH₂CH₂O—<br><br><br>—CH₂CH₂N(H)C(O)O CH₂CH₂O—<br>—CH₂— | U.S. Pat. No. 4,922,004<br>Ma et. al, J. Appl. Pol. Sci., (2014), 131(11), 40352/1-40352/8;<br>WO2016121706 A1<br>U.S. Pat. No. 8,742,175 |
| [acrylate-O-L-phenyl-C(O)-cyclohexyl-OH] | —(CH₂)₅C(O)O—<br>[(CH₂)₅C(O)O]₂—CH₂CH₂O— | U.S. Pat. No. 7,141,354 |
| [acrylate-O-L-phenyl-C(O)-C(OMe)₂-phenyl] | —CH₂CH₂O— | JP 5,310,635 |
| [acrylate-O-L-phenyl-C(O)-C(O)-phenyl] | —CH₂CH₂O— | WO2018159135 |
| [acrylate-O-L-O-C(O)-C(O)-phenyl] | —CH₂CH₂O— | Hu. et al. Chem. Mater. 1997, 9, 3171-3175 |
| [acrylate-O-L-phenyl-C(O)-C(O)-O-Me] | Covalent bond | CN104610541 |
| [acrylate-O-L-phenyl-C(O)-C(CH₃)₂-morpholine] | —(CH₂)₅C(O)O—[(CH₂)₅C(O)O—]₅—CH₂CH₂S—<br>—CH₂CH₂S— | U.S. Pat. No. 7,141,354<br>Angiolini et al. Polymer 1995, 36(21), 4055-60. |
| [acrylate-O-L-thioxanthone] | —CH₂CH₂O— | WO2018159135 |
| [acrylate-O-L-anthraquinone] | —CH₂CH₂CH₂O— | WO2018159135 |
| [acrylamide-NH-L-phenyl-C(O)-phenyl] | Covalent Bond<br>—C(CH₃)₂—C(O)O— | Allen et. al. J. Photochem. Photobiol. A. Chem. 1996, 99, 191-196<br>U.S. Pat. No. 6,245,922 |

-continued

| Structure | L of Formula 1 | Reference |
|---|---|---|
| [acrylate-O-L'-phenyl-C(O)-C(CH₃)₂-OH] | —CH₂CH₂O— / —C(CH₃)₂— C(O)N(H)CH₂CH₂O— | US 2020/0109106 / US 2020/0109106 |
| [acrylamide-NH-L'-phenyl-C(O)-C(cyclohexyl)(OH)] | —CH₂CH₂O— | US 2020/0109106 |
| [acrylamide-NH-L'-phenyl-C(O)-C(O)-O—] | —C(CH₃)₂—CH₂— | US 2020/0109106 |
| [acrylamide-NH-L'-phenyl-C(O)-C(O)-O-ethyl] | —C(CH₃)₂— | US 2020/0109106 |
| [acrylamide-NH-L'-thioxanthone] | —C(CH₃)₂— C(O)OCH₂CH₂O— | U.S. Pat. No. 6,245,922 |

Various (e.g. divalent) organic linking groups, (e.g. L of Formula 1), are represented by these compounds, as set forth in the above table. The (e.g. divalent) organic linking group can be a covalent bond or comprise moieties such as ester, urethane, alkoxy, and alkylene optionally comprising one or more catenary oxygen or sulfur atoms, and combinations thereof. The optionally substituted alkylene group is typically a $C_1$-$C_{12}$ alkylene, and any interval of integers within this range, such as $C_2$-$C_6$.

Some specific organic linking groups (e.g. L of Formula 1) include for example —$R^4$X—, —$R^4$XC(O)—, —$R^4$NHC(O)X—, or —$R^4$NHC(O)X$R^4$X—, wherein X is the same as defined for Formula 1 and $R^4$ is a divalent alkylene optionally comprising one or more catenary oxygens. The optionally substituted alkylene group is typically a $C_1$-$C_{12}$ alkylene, and any interval of integers within this range such as $C_2$-$C_6$.

As evident by Formula 1, there are also organic linking moieties between Rf and X bonded to linking group L. Such moieties include an amide moiety, one or more amine moieties, an alkylene moiety, and a carbonyl moiety.

The organic linking group has a sufficiently low molecular weight such that the fluorinated photoinitiator compound falls within the molecular weight range as will subsequently be described. In some embodiments, the molecular weight of the organic linking groups is no greater than 300, 250, 200, 150, 100 or 75 g/mole.

Compounds comprising an acryl group and a photoinitiator group can be synthesized by reaction of a hydroxy-functional photoinitiator with a hydroxy-reactive acryl compound, such as an isocyanato ($C_1$-$C_4$)alkyl acrylate. One representative hydroxy-functional photoinitiator is 2-hydroxy-4'-(2-hydroxyethoxy)-2-methyl-propiophenone commercially available as IRGACURE 2959, Mw=224 g/mole.

Since the perfluorinated methyl ester reactant comprises a mixture of perfluoroxyalkylene groups of various chain lengths, the resulting (e.g. Michael addition) fluorinated photoinitiator compound also comprises a mixture of perfluorooxyalkylene groups of various chain lengths.

The (e.g. Michael addition) photoinitiator compound (e.g. according to Formula 1) typically has a (e.g. number average) molecular weight of no greater than 5000, 4500, 4000, 3500, 3000, or 2500 g/mole. In some embodiments, the (e.g. number average) molecular weight is no greater than 2200, 2100, 2000, 1900, or 1800 g/mole. In some embodiments, the (e.g. number average) molecular weight is at least 500, 1000, or 1500 g/mole. During the synthesis of the compound, the molecular weight can be calculated by the equivalent weight of the reactants (i.e. amino functional perfluorinated compound and compound comprising an acryl group and a photoinitiator group) as further described in the forthcoming examples. Alternatively, the molecular weight of the (e.g. Michael addition) photoinitiator compound (e.g. according to Formula 1) can be determined by nuclear magnetic resonance (NMR), liquid chromatography optionally followed by NMR, and/or mass spectrometry.

In some embodiments, the (e.g. Michael addition) photoinitiator compound (e.g. according to Formula 1) has an average wt. % fluorine of at least 45, 46, 47, 48, 49, 50, 51, 52, 53, 54, or 55 wt. %. During the synthesis of the compound, the wt. % fluorine can be calculated from the reactants. Alternatively, the wt. % fluorine can be calculated utilizing Combustion Ion Chromatography (CIC) as described in WO2017/172390. In other embodiments, the (e.g. Michael addition) photoinitiator compound (e.g. according to Formula 1) has an average wt. % fluorine of at least 30, 35 or 40 wt. % ranging up to 45 wt. % fluorine.

Photoinitiators with a sufficiently high fluorine content are miscible with highly fluorinated free-radically polymerizable monomers oligomers and mixtures thereof. Less fluorinated compounds can concurrently function as a photoinitiator and a low surface energy additive for less fluorinated and non-fluorinated free-radically polymerizable materials.

The (e.g. Michael addition) photoinitiator compounds (e.g. according to Formula 1) described herein are suitable for use as photoinitiators in a (e.g. photo)polymerizable composition.

Photoinitiators are often characterized according to absorption wavelength maximums or in other words absorption peaks. For example, Irgacure 2959 is reported to have the following absorbance properties:

| Tradename | Chemical Description | Measured Absorbance at 385 nm (1 g/liter) | Measured Absorbance at 365 nm (1 g/liter) | Absorption Peak Wavelength (nm) |
|---|---|---|---|---|
| IRGACURE 2959 Mw = 224 g/mole | 2-hydroxy-4'-(2-hydroxyethoxy)-2-methyl-propiophenone | 0.01 | 0.1 | 273, 330 |

The absorbance of a photoinitiator solution can be determined using a spectrophotometer (according the test method described in the examples). The solvent of the photoinitiator solution is suitable for dissolving the photoinitiator. In typical embodiments, acetonitrile is a suitable solvent. The concentration of photoinitiator dissolved in the solution for determining the absorbance is sufficiently high such that the measured absorbance is greater than the baseline "noise". In typical embodiments, a concentration of 0.01 wt. % or 0.1 wt. % is useful for determining the absorbance properties of a photoinitiator. One of ordinary skill in the art appreciates that there is a linear relationship between absorbance and concentration. Therefore, the absorbance at other concentrations can be calculated.

Figure 2:
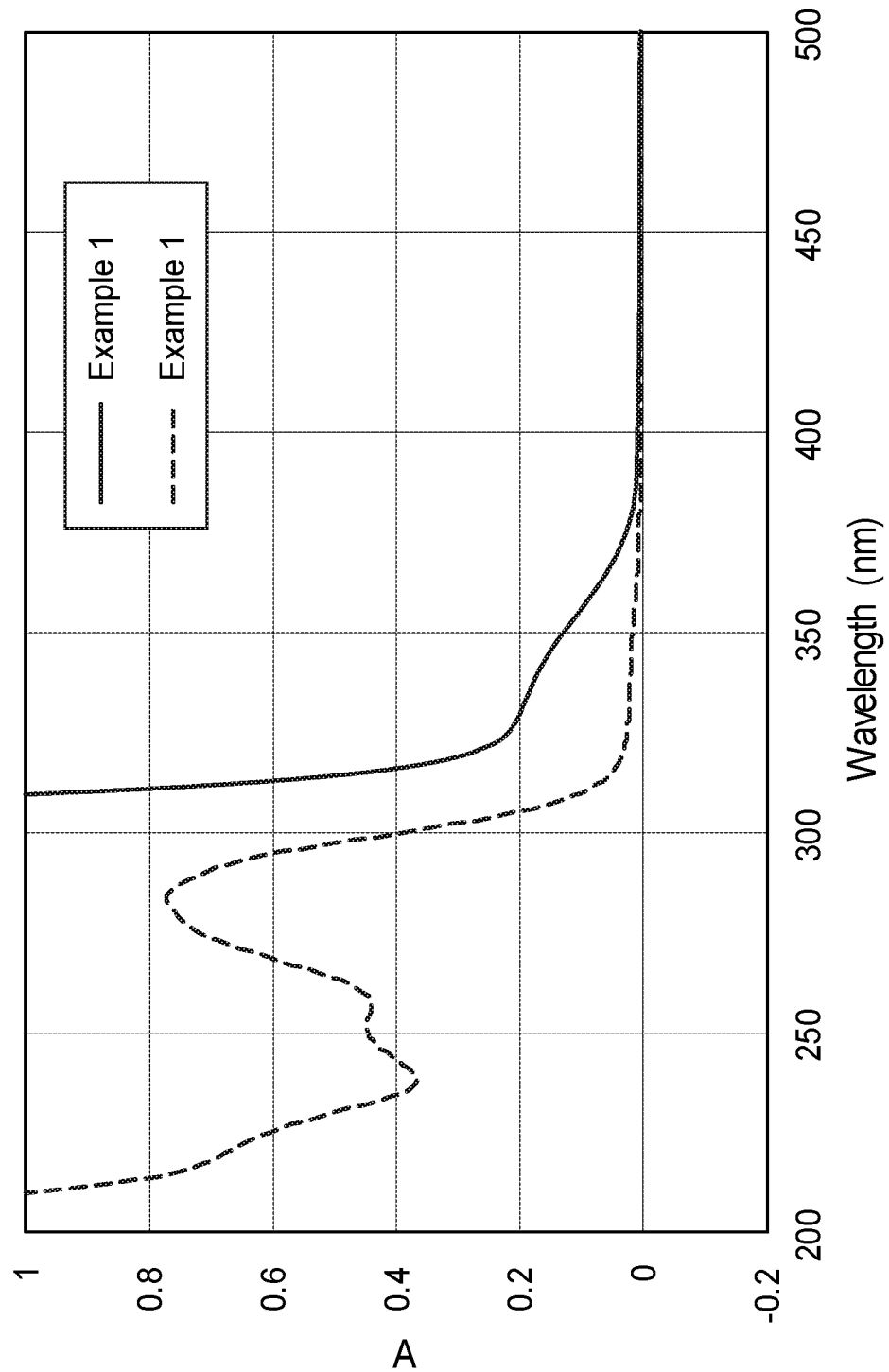
Figure 3:
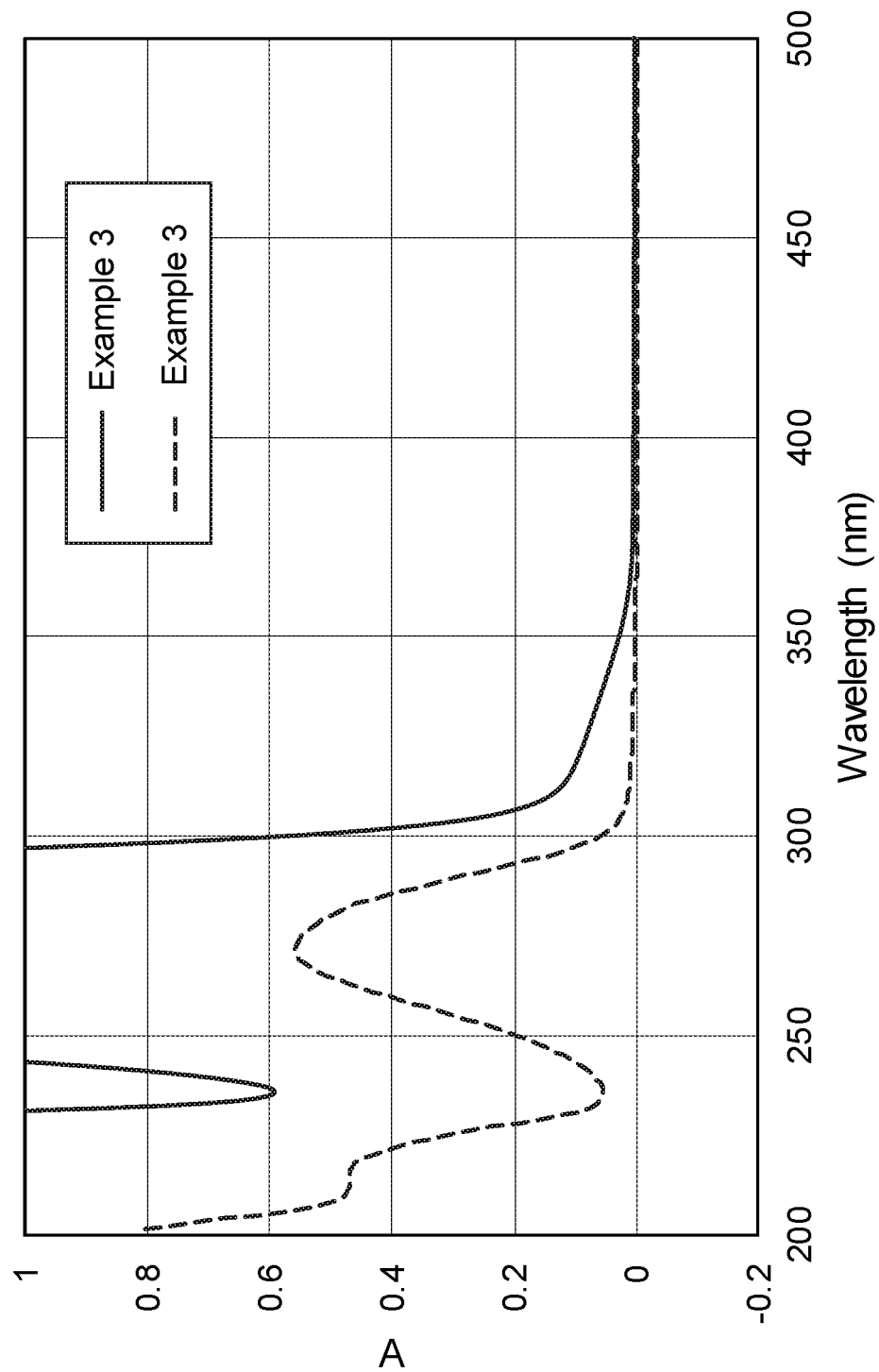

As evident by FIGS. 1-3 the illustrative fluorinated photoinitiator compounds have an absorbance of greater than 0.01, 0.05, 0.10, 0.20, 0.30, 0.40, 0.50, 0.60, 0.70 fora 0.01 wt. % concentration in acetonitrile solution at a pathlength of 1 cm typically at a wavelength in a wavelength range from 250 to 300 nm. The illustrative fluorinated photoinitiator compounds have a peak wavelength within the same range (e.g. about 275 nm).

One of ordinary skill in the art appreciates that other photoinitiator groups will have different absorption properties. Absorption wavelength maximums are reported for various photoinitiators in *Industrial Photoinitiators, A Technical Guide*, W Arthur Green, CRC Press, Taylor and Francis Group, 2010.

In another embodiment, a (e.g. photo)polymerizable composition is described comprising at least one free-radically polymerizable (e.g. acryl) monomer, oligomer, polymer, or combination thereof; and the fluorinated photoinitiator compound, as described herein.

Such photoinitiators are particularly advantageous for use in a polymerizable composition comprising fluorinated free-radically polymerizable monomer(s), oligomer(s), or combinations thereof. In some embodiments, the fluorinated free-radically polymerizable monomer(s), oligomer(s), or combinations thereof have a fluorine content of at least 25, 30, 35, 40, 45, 50, 55, 60, or 65 wt. % and typically less than 75 wt. %.

In typical embodiments, the (e.g. photo)polymerizable composition comprises one or more fluorinated photoinitiator compound in an amount of at least 0.5, 1, 1.5, 2, 2.5, 3, or 3.5 wt. % solids. The amount of fluorinated photoinitiator compound is typically no greater than 15, 10 or 5 wt. % solids. The fluorinated photoinitiator may be a single compound as described herein, a combination of compounds as described herein, or at least one fluorinated photoinitiator as described herein in combination with a different fluorinated photoinitiator, such as described in the literature.

In one embodiment, the fluorinated photoinitiator compound, as described herein, is utilized during the (e.g. photo)polymerization of a fluorinated oligomer comprising a perfluorinated (e.g. perfluorooxyalkyl or perfluorooxyalkylene) group. Suitable fluorinated acrylate monomers and oligomers include mono- and di-(meth)acrylates with molecular weights from about 200-3000 g/mole, including mono- and di-acrylates of perfluoropolyether oligomers, such as described in U.S. Pat. No. 8,658,248.

In one embodiment, the (e.g. photo)polymerizable composition comprises an HFPO oligomer diacrylate such as depicted as follows, where n is selected such that the molecular weight (Mn) is at least 1000, 1500, or 2000 g/mole.

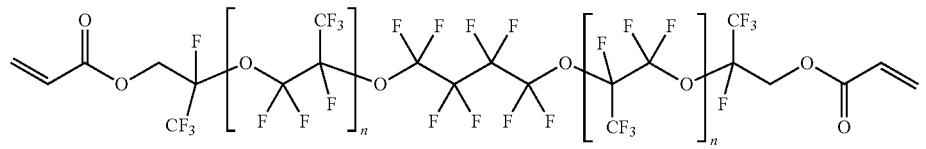

Such HFPO oligomer diacrylate can be fully cured by the fluorinated photoinitiator described herein, as described in greater detail in the examples.

Also described is a method of making a cured composition comprising providing a (e.g. photo)polymerizable composition comprising the fluorinated photoinitiator as described herein; and radiation curing the (e.g. photo)polymerizable composition. In some embodiments, the method further comprises coating the (e.g. photo)polymerizable composition onto a substrate prior to radiation curing. In some embodiments, upon radiation curing the polymerizable composition forms a film or film layer.

In typical embodiments, radiation curing comprises exposing the (e.g. coated) composition to wavelengths of ultraviolet (UV) and visible light.

UV light sources can be of various types. Low light intensity sources, such as blacklights, generally provide intensities ranging from 0.1 or 0.5 mW/cm$^2$ (millwatts per square centimeter) to 10 mW/cm$^2$ (as measured in accordance with procedures approved by the United States National Institute of Standards and Technology as, for example, with a UVIMAP UM 365 L-S radiometer manufactured by Electronic Instrumentation & Technology, Inc., in Sterling, VA). High light intensity sources generally provide intensities greater than 10, 15, or 20 mW/cm$^2$ ranging up to 450 mW/cm$^2$ or greater. In some embodiments, high light intensity sources provide intensities up to 500, 600, 700, 800, 900 or 1000 mW/cm$^2$. UV light can be provided by various light sources such as light emitting diodes (LEDs), fluorescent blacklights, arc-lamps such as xenon-arc lamps and medium and low-pressure mercury lamps (including germicidal lamps), microwave-driven lamps, lasers, etc., or a combination thereof. The composition can also be polymerized with higher intensity light sources as available from Fusion UV Systems Inc. Lamps that emit ultraviolet or blue light are typically preferred. The UV exposure time for polymerization and curing can vary depending on the intensity of the light source(s) used. For example, complete curing with a low intensity light course can be accomplished with an exposure time ranging from about 30 to 300 seconds; whereas complete curing with a high intensity light source can be accomplished with shorter exposure time ranging from about 1 to 20 seconds.

When the (e.g. photo)polymerizable composition comprises cured fluorinated free-radically polymerizable monomer(s), oligomer(s), and combinations thereof, the cured composition can have a low refractive index.

Low refractive index layers may be deposited by a process of vapor coating fluorinated acrylate monomers and/or oligomers, optionally with adhesion promoter(s) and/or photoinitiator(s), and curing by exposure to ultraviolet radiation (UV), electron beam (e-beam), ionizing radiation (gamma rays) or plasma radiation. The adhesion promoter (also referred to as a coupling agent) may be fluorinated or non-fluorinated. Fluorinated coupling agents are described in the literature and also described in concurrently filed US provisional patent application, incorporated herein by reference. The process and articles are described in 81487WO003 PCT/IB2019/059605; 81499WO003 (PCT/US2019/060252); and concurrently filed US provisional patent application; incorporated herein by reference.

TABLE 1

Materials

| Material designation | Description |
|---|---|
| AEBP | Acrylated ethyoxyethyl benzophenone, CAS 22421-66-5, prepared as in U.S. Pat. No. 9,587,127, Examples 5 and 6, columns 11 and 12. |
| BHT | 2,6-di-t-butyl-4-methylphenol obtained from Alfa Aesar, Haverhill, MA. |
| Ethyl acetate | Obtained from EMD Millipore, a part of Merck KGaA, Billerica, MA. |
| HFPO—C(O)NH—CH$_2$CH$_2$CH$_2$—NH(CH$_3$) | Prepared by a method similar to that of Preparation 22, as shown in U.S. Pat. No. 7,718,264 column 29, lines 44-57. |
| 4-hydroxy-TEMPO | 4-Hydroxy-2,2,6,6-tetramethylpiperidine 1-oxyl, CAS 2226-96-2, obtained Sigma Aldrich, St. Louis, MO. |

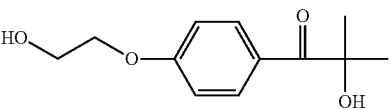

| | |
|---|---|
| IEA | Isocyanatoethyl acrylate, MW 144.12, available under the trade designation "KARENZ AOI," from Showa Denko. |
| Irgacure 2959 | 2-hydroxy-4'-(2-hydroxyethoxy)-2-methylporpionphenone, CAS 106797-53-9, obtained from TCI America, Portland, OR. |

| | |
|---|---|
| Methyl ethyl Ketone (MEK) | Obtained from EMD Millipore, a part of Merck KGaA |
| 3-(methyl)-1,3-propane diamine | CAS number 6291-84-5, obtained Sigma Aldrich, St. Louis, MO. |
| Novec 7200 | C$_4$F$_9$OCH$_2$CH$_3$, obtained from 3M Company, St Paul, MN. |

TABLE 1-continued

Materials

| Material designation | Description |
| --- | --- |
| HFPO Oligomer Diacrylate Mn = 2000 g/mol | 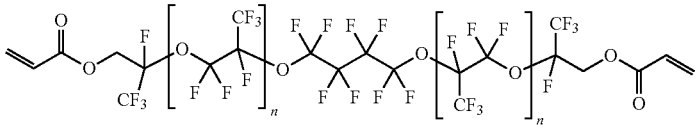 Prepared according to the synthetic method generally described in U.S. Pat. No. 9,718,961. (PFE-3) |

Preparation 1. Intermediate—(CH$_3$)NH—CH$_2$CH$_2$CH$_2$NH(O)C—HFPO—C(O)NH—CH$_2$CH$_2$CH$_2$—NH(CH$_3$)

CH$_3$(O)C—HFPO—C(O)CH$_3$, 50 g (651.485 number average equivalent weight, 0.076748 eq), prepared in a manner similar to that for Preparation No. 26, U.S. Pat. No. 7,718,264 Column 30, lines 41-53, and 3-(methyl)-1,3-propane diamine 6.77 g (0.076748 eq) was added to a 250 mL flask equipped with stirbar, and stirred at room temperature under nitrogen for about 1.5 h, at which time an aliquot was taken for Fourier Transform Infrared (FTIR) analysis, which showed disappearance of the ester doublet at about 1800 and 1780 cm$^{-1}$ (small, large) and appearance of an amide band at about 1718 cm$^{-1}$. The material was concentrated on a rotary evaporator at 1.5 torr for 30 min, yield 53.84 g of a thick oil.

Preparation 2. Example 1

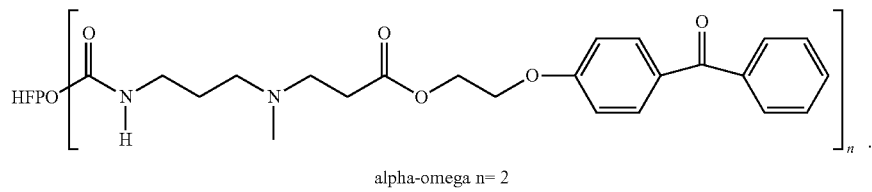

alpha-omega n= 2

From Preparation 1, (CH$_3$)NH—CH$_2$CH$_2$CH$_2$NH(O)C—HFPO—C(O)NH—CH$_2$CH$_2$CH$_2$—NH(CH$_3$), 12.54 g (0.0177 eq, 707.63 number average EW) and AEBP 5.00 g (0.0169 eq., 296.31 EW) in 5 g of ethyl acetate were mixed with an additional 5 g of ethyl acetate in a 250 mL flask equipped with stir bar under dry air, and after 17 h an aliquot was analyzed by $^1$H Fourier Transform Nuclear Magnetic Resonance (FT-NMR), showing about 8-9% of olefin remaining. Next, (CH$_3$)NH—CH$_2$CH$_2$CH$_2$NH(O)C—HFPO—C(O)NH—CH$_2$CH$_2$CH$_2$—NH(CH$_3$), 1.00 g (0.000678 eq) and 5 g more ethyl acetate were added, and after reaction overnight, analysis by $^1$H FT-NMR showed no olefin remaining. The material was concentrated on a rotary evaporator at aspirator pressure and then at 3 torr for 30 min to provide 18.53 g of a low melting gel.

In view of the additional of HFPO—[C(O)NH—CH$_2$CH$_2$CH$_2$—NH(CH$_3$)] required to react with two equivalents of AEBP, the stoichiometric equivalent weight of the HFPO—[C(O)NH—CH$_2$CH$_2$CH$_2$—NH(CH$_3$)] was determined to be 802.40 (1604.80 MW). Therefore, the total molecular weight of the compound of Example 1 was 2197.44 g/mole and Example 1 had 43.3% fluorine by weight.

Preparation 3. Example 2

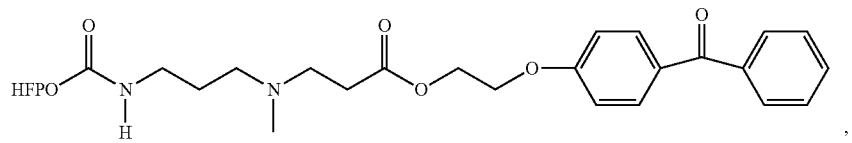

AEBP (296.31 MW, 0.05062 mol) and HFPO—C(O)NH—CH₂CH₂CH₂—NH(CH₃) 66.24 g (1246.15 number average MW, 0.0532 mol), were dissolved with heat in 90.2 g of ethyl acetate and 81.0 g of Novec 7200 in a 500 mL flask equipped with magnetic stir bar under dry air, and allowed to stir at room temperature overnight. An aliquot was removed for $^1$H FT-NMR and analysis showed that about 20-24 mole percent of olefin remained, and 20 mole percent more (13.25 g) HFPO—C(O)NH—CH₂CH₂CH₂—NH(CH₃) was added. After 3 additional days at room temperature, $^1$H FT-NMR and analysis showed that no olefin remained. To the reaction was added 0.169 g 4-hydroxy TEMPO (1790 ppm), and the reaction was concentrated at 35° C. to remove most of the Novec 7200, and then at up to 85° C. at 1.3 torr (slowly increasing vacuum to avoid foaming) to provide 92.9 g of a material that cooled to a soft gel.

In view of the additional of HFPO—[C(O)NH—CH₂CH₂CH₂—NH(CH₃)] required to react with one equivalent of AEBP, the stoichiometric equivalent weight of the HFPO—[C(O)NH—CH₂CH₂CH₂—NH(CH₃)] was determined to be 1570.20 g/mole. Therefore, the total molecular weight of the compound of Example 2 was 1866.51 g/mole and Example 2 had 54.3% fluorine by weight.

Preparation 4. Intermediate

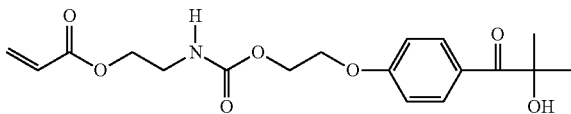 [SMILES: C=CC(=O)OCCNC(=O)OCCOc1ccc(C(=O)C(C)(C)O)cc1]

Irgacure 2959, 50.00 g (0.223 mol, 224.26 MW) was charged to a 250 mL flask equipped with stir bar, followed by 250.00 g of MEK under dry air. The Irgacure 2959 did not completely dissolve, and 0.0322 g (400 ppm based on total solids) BHT and 0.008 g (100 ppm based on total solids) 4-hydroxy TEMPO were added. Next, 30.52 g (0.216 mol, 141.12 MW) IEA was added via a pressure equalizing addition funnel, reaching a maximum temperature of 34° C. at about 40 min. Addition was complete at 1.75 h, at which time analysis of an aliquot showed a small —NCO peak at 2265 cm$^{-1}$. After stirring overnight, FTIR showed no —NCO peak. The material was concentrated at 45° C. under aspirator pressure for about 1.5 h, then at 50° C. for at 4 torr for about 30 min, yielding 81.74 g of a material that solidified to a white solid.

Preparation 5. Example 3

The product of Preparation 4, 5.00 g (0.0137 mol, 365.38 MW), and 17.91 g (0.0144 mol, 1246.15 number average MW) HFPO—C(O)NH—CH₂CH₂CH₂—NH(CH₃), along with 25 g of Novec 7200 and 10 g ethyl acetate were added to a 100 mL flask equipped with stir bar under dry air. The reaction, initially cloudy, cleared after 2 h of mixing at room temperature. After 3 days of mixing at room temperature, analysis of an aliquot by $^1$H FT-NMR showed that about 5 mole percent olefin remained, and 0.95 g (0.00072 mol) HFPO—C(O)NH—CH₂CH₂CH₂—NH(CH₃) was added. After stirring overnight, $^1$H FT-NMR and analysis of an aliquot showed that no olefin remained. The reaction was concentrated on a rotary evaporator for about 30 min at aspirator pressure and at 69° C. for about 30 min at 3 torr to yield 23.25 g of a material that solidified to a white solid.

In view of the additional of HFPO—[C(O)NH—CH₂CH₂CH₂—NH(CH₃)] required to react with one equivalent of AEBP, the stoichiometric equivalent weight of the HFPO—[C(O)NH—CH₂CH₂CH₂—NH(CH₃)] was determined to be 1377.88 g/mole. Therefore, the total molecular weight of the compound of Example 2 was 1743.26 g/mole and Example 2 had 50.5% fluorine by weight.

UV-VIS Measurements of Photoinitiators 0.1 wt. % and 0.01% wt. % solutions of the fluorinated photoinitiator acetonitrile were prepared. Spectrophotometer cuvettes were filled with the solutions. A Lambda 365 UV-Vis spectrometer (PerkinElmer, Waltham, MA) was used to measure the UV-VIS spectrum of photoinitiator solutions at a 10 mm pathlength. UV-VIS absorbances as a function of wavelength of the compounds of Examples 1-3 are depicted in FIGS. 1-3

Curing Effectiveness

An evaluation of the curing effectiveness of the materials was done by spin-coating a mixture of HFPO oligomer diacrylate and the fluorinated photoinitiator material(s) at varying concentrations onto an unprimed PET substrate (Weinview SC100, 3000 RPM, 10 sec). The HFPO oligomer diacrylate and fluorinated PI mixtures were diluted in a solvent (Novec 7200 or 1,1,1-trifluorotoluene, 1:4) to yield a "dry" thickness of approximately 1-2 micrometers. Immediately after spin-coating, the samples were transferred to a conveyor belt and exposed to UVC germicidal lamps (12) in a water-cooled, nitrogen-purged enclosure. The UVC lamps were allowed to warm up and stabilize for thirty minutes prior to dosimetry characterization and spin-coating. UV dosimetry was completed using an EIT Power Puck II (EIT, Leesburg, VA): the measured peak irradiance was 10 mW/cm², and a line speed of 7 feet per minute (2.13 m/min) was chosen to yield a UVC dose of 54 mJ/cm². If the deposited film was not completely cured, as determined by the criteria listed in Table 2 below, the film was exposed

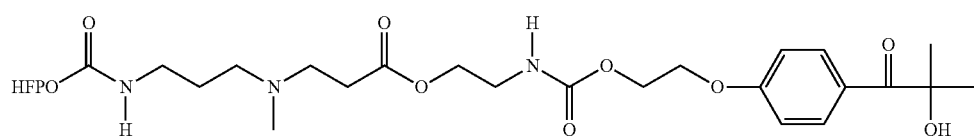

again to the UVC light until the film was completely cured, or the film had not completely cured after six sequential passes.

The curing effectiveness, or level of cure, of the cured film was evaluated qualitatively according to the following criteria:

| Level of Cure | Explanation/Description |
|---|---|
| NO CURE (N) | deposited film is easily removed from substrate (completely liquid or substantially liquid) |
| PARTIAL (P) | deposited film has solidified but is able to be removed or smudged (gel) |
| COMPLETE (C) | deposited film is substantially solid and mechanically robust, not able to be removed or smudged (solid) |

| Photoinitiator | PI Amount (wt. % solids) | Number of UV Exposures (54 mJ/cm² UVC per exposure) | | | | | | Comments |
|---|---|---|---|---|---|---|---|---|
| | | 1 | 2 | 3 | 4 | 5 | 6 | |
| Example 2 | 2.8 | C | | | | | | |
| | 7.6 | P | C | | | | | |
| Example 1 | 7.7 | N | N | N | N | N | N | low miscibility (required vigorous mixing in solvent) |
| | 14.6 | N | N | N | N | N | N | low miscibility (required vigorous mixing in solvent) |
| Example 3 | 3.3 | C | | | | | | |
| | 5.6 | C | | | | | | |
| | 13.0 | C | | | | | | |

Although Example 1 had low miscibility with the HFPO oligomer diacrylate, Example 1 is surmised to be compatible with free-radically polymerizable monomer and oligomers having a lower fluorine content. Further Example 1 can concurrently function as a photoinitiator and a low surface energy additive for less fluorinated or non-fluorinated free-radically polymerizable materials.

What is claimed is:

1. A compound having the formula $$R_f—[C(O)NH—R^1—N(R^2)—CH_2CH_2—C(O)—X-L-PI)]_n$$

wherein
- $R_f$ is a monovalent perfluorooxyalkyl group or divalent perfluorooxyalkylene group;
- $R^1$ is an alkylene group optionally containing one or more catenary oxygen atoms,
- $R^2$ is H or an alkyl group of 1 to 4 carbon atoms,
- X is —O—, —S—, or —NR³—, wherein $R^3$ is H or an alkyl group of 1 to 4 carbon atoms,
- L is a covalent bond or divalent organic linking group;
- PI is a photoinitiator group;
- n is 1 when $R_f$ is a monovalent perfluorooxyalkyl group or n is 2 when $R_f$ is a divalent perfluorooxyalkylene group.

2. The compound of claim 1 wherein the divalent organic linking group comprises moieties selected from ester, urethane, alkoxy, and alkylene optionally containing one or more catenary oxygen or sulfur atoms, and combinations thereof.

3. The compound of claim 1 wherein the photoinitiator group comprises a phenone group.

4. The compound of claim 3 wherein the photoinitiator group is selected from benzophenone and acetophenone.

5. The compound of claim 1 wherein the compound has a number average molecular weight of no greater than 5000, 4500, 4000, 3500, 3000, 2500, or 2000 g/mole.

6. The compound of claim 1 wherein the compound has an average wt. % fluorine of at least 30, 35, or 40 wt. %.

7. A polymerizable composition comprising at least one free-radically polymerizable monomer, oligomer, or combination thereof, and a fluorinated photoinitiator compound comprising a perfluorinated group bonded to at least one terminal photoinitiator group with an organic linking group comprising at least one amide moiety.

8. The composition of claim 7 wherein the free-radically polymerizable monomer, oligomer, or combination thereof is fluorinated.

9. The composition of claim 8 wherein the free-radically polymerizable monomer, oligomer, or combination thereof has a fluorine content of at least 25, 30, or 35 wt. %.

10. The polymerizable composition of claim 7 wherein the composition comprises an oligomer having a perfluorooxyalkylene group.

11. A method of making a cured composition comprising: providing the polymerizable composition of claim 7; and radiation curing the photopolymerizable composition.

12. The method of claim 11 wherein the radiation curing comprises exposing the composition to wavelengths of ultraviolet light.

13. The method of claim 11 further comprising coating the polymerizable composition onto a substrate prior to radiation curing.

14. The method of claim 11 wherein upon radiation curing the polymerizable composition forms a film or film layer.

15. The polymerizable composition of claim 7 wherein the compound has the formula $$R_f—[C(O)NH—R^1—N(R^2)—CH_2CH_2—C(O)—X-L-PI)]_n$$

wherein
- $R_f$ is a monovalent perfluorooxyalkyl group or divalent perfluorooxyalkylene group;
- $R^1$ is an alkylene group optionally containing one or more catenary oxygen atoms,
- $R^2$ is H or an alkyl group of 1 to 4 carbon atoms,
- X is —O—, —S—, or —NR³—, wherein $R^3$ is H or an alkyl group of 1 to 4 carbon atoms,
- L is a covalent bond or divalent organic linking group;

PI is a photoinitiator group;

n is 1 when $R_f$ is a monovalent perfluorooxyalkyl group or n is 2 when $R_f$ is a divalent perfluorooxyalkylene group.

16. The polymerizable composition of claim 15 wherein the photoinitiator group comprises a phenone group.

17. The polymerizable composition of claim 16 wherein the photoinitiator group is selected from benzophenone and acetophenone.

18. The polymerizable composition of claim 7 wherein the compound has a number average molecular weight of no greater than 5000, 4500, 4000, 3500, 3000, 2500, or 2000 g/mole.

19. The polymerizable composition of claim 7 wherein the compound has an average wt. % fluorine of at least 30, 35, or 40 wt. %.

* * * * *